United States Patent [19]

Drizen et al.

[11] Patent Number: 5,709,883
[45] Date of Patent: Jan. 20, 1998

US005709883A

[54] LONG ACTING NARCOTIC ANALGESICS AND ANTAGONISTS

[75] Inventors: Alan Drizen; Peter Rothbart, both of Ontario, Canada; Gary M. Nath, Bethesda, Md.

[73] Assignee: L.A.M. Pharmaceuticals, LLC, Miami, Fla.

[21] Appl. No.: 787,396

[22] Filed: Jan. 22, 1997

Related U.S. Application Data

[60] Division of Ser. No. 630,205, Apr. 10, 1996, which is a continuation-in-part of Ser. No. 536,750, Sep. 29, 1995.

[51] Int. Cl.⁶ .................................................. A61K 9/08
[52] U.S. Cl. .................................. 424/488; 424/426
[58] Field of Search ................................ 424/488, 426, 424/425

[56] References Cited

U.S. PATENT DOCUMENTS

| | | | |
|---|---|---|---|
| 5,143,724 | 9/1992 | Leshchinec et al. | 424/78.08 |
| 5,356,629 | 10/1994 | Sander et al. | 424/422 |
| 5,358,973 | 10/1994 | Linblad et al. | 424/488 |
| 5,540,912 | 7/1996 | Roorda et al. | 424/426 |
| 5,587,175 | 12/1996 | Viegas et al. | 424/488 |
| 5,599,552 | 2/1997 | Dunn et al. | 424/425 |
| 5,614,221 | 3/1997 | Fjellström | 424/488 |
| 5,631,011 | 5/1997 | Wadström | 424/426 |
| 5,631,015 | 5/1997 | Bezwada et al. | 424/426 |

*Primary Examiner*—Amy Hulina
*Attorney, Agent, or Firm*—Nath & Associates; Gary M. Nath

[57] ABSTRACT

Long acting narcotic compositions comprising a water-soluble analgesic or antagonist drug dispersed within a polymer matrix, methods of producing the same and treatments with the complex.

9 Claims, No Drawings

LONG ACTING NARCOTIC ANALGESICS AND ANTAGONISTS

RELATED APPLICATION(S)

This application is a Divisional Application of U.S. patent application Ser. No. 08/630,205, filed Apr. 10, 1996, which is a continuation-in-part application of U.S. patent application Ser. No. 08/536,750 filed Sep. 29, 1995, the contents of which are incorporated herein in their entirety.

BACKGROUND OF THE INVENTION

1. Field of the Invention

This invention relates to the preparation of long acting analgesics, and more particularly to a water-soluble system for the intramuscular administration of a narcotic drug. The system is designed to administer effective levels of drugs over a sustained period of time when administered intramuscularly, for the treatment of pain and drug addiction.

2. Description of the Prior Art

Medications have been formulated to enable the administration of drugs to occur over a wide variety of paths, including instantaneous delivery by use of injectables, and sustained, controlled and extended release delivery by controlling a drugs delivery rate, such as by resistance of a structure's coating or composition against diffusion of the drug therethrough. These systems have all found wide applications for the delivery of drugs.

None of the known drug delivery systems, however, are able to administer effective therapeutic amounts of an analgesic drug for sustained periods of time, that is, longer than 12 to 48 hours without repeated administration of the drug every 2 to 5 hours. Drugs that have been repeatedly administered for long term treatments include but are not limited to analgesics and antagonists for treating pain.

Morphine and drugs having similar structures, especially opioids, have been used for pain relief, and primarily treatment of nociceptive pain, namely that due to irritation or damage of pain receptors in the skin or nearby tissues. Examples of such narcotics include morphine sulfate, Dilaudid, Demerol, codeine, Taliwin and Percocet.

The problems associated with narcotic use are manifold, but primarily relate to their relative short duration for pain relief, namely two to five hours with intramuscular injection, and secondly, they are addictive, especially when used in large doses. Tolerance and physical dependence on both natural and synthetic opioids develops rapidly; therapeutic doses taken regularly over a two or three day period can lead to some tolerance and dependence, and the user may show symptoms of withdrawal when the drug is discontinued. Furthermore, opioid drugs induce cross-tolerance and abusers may substitute one drug for another.

Currently, analgesics are used to treat various pain conditions in several ways.

(1) intramuscular or oral administration of morphine, Dilaudid or codeine with repeated injections every two to five hours;

(2) patient controlled analgesia where the patient operates an intravenous drip with control of the amount of drug by a computer delivery procedure where small amounts are administered on demand; and (3) continuous epidural pump infusions where the analgesic is administered by a computerized pump through tubing into the epidural space and wherein the dose is continuously adjusted.

A delivery system is therefore needed which would permit the administration of therapeutically effective amounts of analgesic and antagonist drugs to enable a continued and sustained release for at least 12 hours to several days.

SUMMARY OF THE INVENTION

The present invention relates to the formation of long-acting analgesic and antagonist composition for use in treating acute or chronic pain conditions and aiding in treating drug addiction. More particularly, this invention relates to an injectable narcotic drug solubilized in a liquid polymer matrix, with or without the presence of a preservative. The polymer matrix is composed of a negatively charged polymer material selected from the group consisting of polysulfated glucosoglycans, glycosaminoglycans, mucopolysaccharides and mixtures thereof, and a nonionic polymer selected from the group consisting of carboxymethylcellulose sodium, hydroxyethyl cellulose, hydroxypropyl cellulose, and mixtures thereof.

Another embodiment of this invention involves a method for the treatment of a condition in animals, which comprises intramuscularly injecting therapeutically effective doses (which may be less than the normal therapeutic dosage) of a solution of a narcotic solubilized drug within an aqueous liquid containing a polymer matrix. Preferably one of the polymer materials has a mean average molecular weight below about 800,000, and the other polymer is a nonionic cellulose derivative.

An alternate embodiment relates to the use of the present formulations to treat drug addiction.

DETAILED DESCRIPTION OF THE INVENTION

The present invention relates to the formation of a delivery system for the intramuscular administration of an analgesic drug for a sustained period, and particularly to its use with a polymer matrix for treatment of acute or chronic intractable pain, and treatment of drug addiction. The process involves the production and use of a specialized delivery system manufactured by using polymers of molecular weights below about 800,000 for the creation of specially modified molecules to treat a variety of conditions. Specifically, the invention involves a process for manufacturing a polymer matrix solubilized in water with various narcotic drugs. The polymers must be sterilizable and acceptable for animal and human use. In this way, a suitable polymer system is formed as a matrix which is able to disperse a much lower molecular weight drug to form a solution of the active for subsequent use.

It has been found in conventional narcotic and anesthetic drug treatments that once a therapeutic dosage is used, the beneficial effect of such dosage routine wears off within several hours of its initial application, thus requiring repetitive treatment. In the case of narcotics, this generally occurs within two to five hours and specifically three to four hours after injection. This mechanism is common in all animal systems and involves biochemical pathways that have not yet been fully discovered or identified. One possibility for this action would involve the animals own immunoglobin system which may be responsible for identifying the presence of the chemical entity and systematically destroying it. Another may be the inherent instability of the chemical entity after its administration into the animal.

It has been unexpectedly discovered that an effective therapeutic level of an analgesic or antagonist drug may be administered once over at least a 12 to 24 hour period to several day interval when the drug is suspended or entrapped in a specially designed polymer matrix containing almost equal molar ratios of a negatively charged polymer and a nonionic polymer dissolved in water.

This system is believed to form a matrix which microencapsulates, suspends and/or entraps the drug entity such that when it is administered it is slowly released into the systemic circulatory system or muscular tissue providing a sustained and prolonged drug release rate.

The molar ratio of the polymers present in the matrix are critical in this invention. It has been found that molar ratios of the negatively charged polymer to the nonionic polymer must be from about 1:0.5 to 2 and preferably from about 1:0.8 to 1.5 and most preferably from about 1:1 to 1.3. At ratios either higher or lower than these levels, the resulting systems tend to sheer when being prepared and form unacceptable air pockets and bubbles. Furthermore, the solutions tend to separate and form distinct polymer layers.

At least one of the polymers used to form the matrix of this invention must be sufficiently negatively charged to aid in the dispersion, encapsulation or solubilization of the analgesic or antagonist drug. Particularly preferred polymers have mean average molecular weights below about 800,000 and preferably molecular weights between about 500,000 to 800,000 have been found acceptable to form useable polymer matrixes. Polymers with mean average molecular weights between about 700,000 and 775,000 are most preferred. Polymers having molecular weights above about 800,000 form solid gels in solution and are unable to serve in an injectable system. Furthermore, the polymers must be sterilizable and be stable during sterilization so that the polymer does not lose molecular weight once formulated into the final injectable form.

Exemplary, non-limiting examples of compounds that may be used as a source of this molecular weight polymer include polysulfated glucosoglycans, glucosaminoglycans, and mucopolysaccharides, derivatives thereof and mixtures thereof. Particularly preferred mucopolysaccharides are chondroitin sulfate and hyaluronic acid salts with sodium hyaluronate being most preferred.

Hyaluronic acid (HA) occurs naturally in joint synovial fluid, where it plays a lubricating role, and may have biological activity as well. HA is a mucopolysaccharide, and may alternatively be referred to as a glycosaminoglycan. The repeating unit of the hyaluronic acid molecule is a disaccharide consisting of D-glucuronic acid and N-acetyl-D-glucosamine. Because hyaluronic acid possesses a negative charge at neutral Ph, it is soluble in water, where it forms highly viscous solutions. The D-glucuronic acid unit and N-acetyl-D-glucosamine unit are bonded through a glycosidic, beta (1–3) linkage, while each disaccharide unit is bonded to the next disaccharide unit through a beta (1–5) linkage. The beta (1–5) linkages may be broken through hydrolysis with the enzyme hyaluronidase.

A variety of substances, commonly referred to as hyaluronic acid, have been isolated by numerous methods from various tissue sources including umbilical cords, skin, vitreous humour, synovial fluid, tumors, haemolytic streptocci pigskin, rooster combs, and the walls of veins and arteries. It is also being synthesized artificially and by recombinant technology.

Conventional methods for obtaining hyaluronic acid results with a product having differing properties and a wide range of viscosities. U.S. Pat. No. 2,585,546 to Hadian, discloses an example of a method for obtaining hyaluronic acid which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or other usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two phases with a precipitate of hyaluronic acid at the interface.

U.S. Pat. No. 4,517,296 to Bracke et al. is directed to the preparation of hyaluronic acid in high yield from streptococcus bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

One particular fraction of hyaluronic acid (HA) that exhibits excellent matrix formation according to the present invention is hyaluronate sodium having a molecular weight of between 650,000–800,000, preferably 700,000–775,000 with a high degree of purity, 95–105% free, and preferably at least 98% pure, from contamination of related mucopolysaccharides. Furthermore, this hyaluronic acid has a sulphated ash content of less than 15% and a protein content of less than 5%. Examples of usable base salts include those safe for animal and human use, such as sodium, potassium, calcium, and magnesium salts or the like.

In contrast to HA, chondroitins are mucopolysaccharides comprising repeating units of D-glucuronic acid and N-acetyl-D-galactosamine. Chondroitin sulphates are important components of cartilage and bone and are excellent for preparing the polymer matrix herein.

The negatively charged polymers are generally present in the system in amounts which enable a solution to be formed. Generally, solutions are formed using amounts of about 0.1 to 2.0% by weight with amounts of about 1 to about 1.5% by weight being preferred for use as an injectable. A particularly preferred sodium HA concentration as an injectable is about 1.2% to about 1.4% by weight of the system.

In addition to the negatively charged polymers, the polymer matrix must contain a nonionic polymer which aids in retarding the rate of absorption of the narcotic drug and delays or slows down an animal's natural absorption of the negatively charged polymer. Without the presence of this component, the drug would be rapidly absorbed, and sustained action of the active could not be achieved. Particularly preferred nonionic polymers are cellulose derivatives and particularly those selected from the group consisting of carboxymethylcellulose sodium, hydroxyethyl cellulose, hydroxypropyl cellulose and mixtures thereof with hydroxyethyl cellulose (HEC) being preferred. These particular polymers have been found to possess exceptional ability to form sustained release matrix formulations when used in combination with a negatively charged polymer. Such polymers are generally employed in amounts of about 0.1% to about 1.5% and preferably about 0.5 to about 1.4%. Amounts above about 1.4% result in the formation of a solid gel product when used with the negatively charged polymer. Amounts below about 0.1% have not been found suitable to prepare a storage stable solution or form a product that has sustained drug release. A particularly preferred HEC concentration is about 1.2% to about 1.3% by weight of the system.

A wide variety of analgesics and antagonist drugs which are administered by injection may be used in the delivery system according to the invention.

One particular criteria of the drug is that they must be solubilized in the polymer matrix solution in order to be injected intramuscularly. Without limitation, this includes analgesics and antagonists that are relatively water-soluble, that is, soluble enough to be dissolved or suspended in the polymer matrix solution so that they may be administered by injection. Particularly preferred drugs include, without limitation, analgesics such as morphine and its salts, such as morphine sulfate, codeine, meperidine, methadone, propoxyphene, levophanol, hydromorphone, oxymorphone, oxycodone, as well as opioid antagonists and agonist-antagonists such as naloxone, naltyhexone, pentazocaine, butorphanol, nalbuyphine, and buspprenorphine. The equianalgesic doses of exemplary opioid analgesics for severe pain is set forth in TABLE I derived from the 16th Edition of the Merck Manual, page 1414. Besides these drugs, exemplary nonlimiting drugs also include:

TALWIN® (pentazocaine lactate) which chemically is 1,2,3,4,5,6-hexahydro-6, 11-dimethyl-3-(3-methyl-3butenyl)-2, 6-methano-3-benzanocin-8-ol lactate.

DEMEROL® (meperidinehydrochloride) which chemically is 1-methyl-4-phenylisonipecolate hydrochloride.

Methadone Hydrochloride which chemically is 3-heptanone, 6-(dimethylamnino)-4,4-diphenyl-, hydrochloride.

LEVO-DROMORAN® also known as levorphanol tartrate.

BUPROENEX® (buprenorphine hydrochloride) which chemically is 17-(cyclopropylmethyl)-α-(1,1-dimethylethyl)-4, 5-epoxy-18, 19-dihydro-3-hydroxy-6-methoxy-α-methyl-6, 14-ethenomorphinan-7-methanol, hydrochloride [5α,7α(S)].

MSIR® (morphine sulfate) which chemically is 7,8 didehydro-4,5-α-epoxy-17-methyl-morphinian-3,6 α-diol sulfate (2:1)(salt) pentahydrate.

DILAUDID® also known as hydromorphone hydrochloride.

SUFENTA® (sufentanil citrate) which chemically is N-[-4-(methyoxymethyl) (-1-[2-(2-thienyl) ethyl]-4-piperidinyl]-N-phenylpropanamide 2-hydroxy-1,2,3,-propanetricarboxylate.

SUBLIMAZE® (fentanyl citrate) which chemically is N-(1-phenethyl-4-piperidyl) propionanilide citrate.

AFENTA® (afentanil hydrochloride) which chemically is N-[1-[2-(4-ethyl-4, 5-dihydro-5-oxo-1H-tetranol-1-yl) ethyl]-4- (methoxymethyl)-4-piperidinyl]-N-phenyl propanamide monohydrochloride.

PERCOCET® which is a combination of oxycodone hydrochloride and acetaminophen.

NUMORPHAN® (oxymorphone hydrochloride) which chemically is 4,5 α-Epoxy-3,14-dihydrox-17-methylmorphinon-6-one hydrochloride.

The polymer solutions of the present invention may be prepared in a variety of ways. For example, the polymers may be dissolved in water and purified either separately or jointly and then the active drug added to the system.

A particularly preferred procedure involves separately dissolving the nonionic polymer in water and centrifuging the material to form a solution and remove impurities. This may be conveniently done at rotation speeds of 2000 rpm for times of about 30 minutes to about two hours.

In contrast, the charged polymer may be blended and stirred in water until it is dissolved. This process must be done while avoiding the formation of bubbles and while freeing the polymer of its electrostatic activity. Furthermore, the molecular weight of the polymer must not be significantly changed during processing and as such mild process conditions are required. Processing conditions of 400–600 rpm for durations of 16–24 hours have been found acceptable to produce stable solutions or gels of the charged polymer.

Once the solutions are prepared, they may be mixed together and blended at moderate speeds to produce a homogenous solution (400–600 rpm for several hours). This solution may then be sterilized, such as by heat at 121° C. for 20 minutes or by other conventional sterilization procedures. After sterilization, the solution may be stored for future use or immediately blended with the analgesic or antagonist drug.

Conventional pharmaceutically acceptable emulsifiers, suspending agents, antioxidants (such as sodium metabisulfate) and preservatives may then be added to this system. Once all the components are blended together, such as by mixing 400–600 rpm for one to four hours, the system is filled into tubes and sterilized. The resulting system is a clear solution which is storage stable for several years.

As indicated above, the drugs may be blended with the aqueous polymer matrix at the time of manufacture or simply mixed together, such as by shaking, at the time of use. As such, the drug when in the form of a water-soluble solid is simply diluted with sterilized water or polymer matrix solution, dissolved and immediately injected into the patient. Alternatively, previously prepared solutions of the drug are blended with the polymer matrix solution, such as in a syringe or the cartridges already containing the solutions, and then injected into the patient. These procedures enable the use of commercially prepared narcotic dosage forms without need for separate processing, handling or storage procedures.

The present long acting narcotic delivery system enables the use of reduced levels of narcotics to be administered over a given period of time which does not cause the highs and lows associated with the two to five hour doses. It also is very likely to decrease the potential for drug addiction by reducing the level of doses required to reduce the pain. In this regard, it has been found that use of a single or multiple amount of a single dose (of a conventional dosage) administered once every 24 hours when mixed with the aqueous polymer matrix will achieve the same effect as six to ten conventional doses administered every two to five hours of duration.

The injection of a single daily dose is extremely easy and safe to administer and obviates the need for machinery maintenance (pump devices), continuous nursing care monitoring and dosage recalculation associated with epidural pumps.

The dosage system can be formed with or without the use of pharmaceutically acceptable preservatives. A significant advantage of the dosage form of the present system relates to its ability to allow the drug to slowly diffuse through tissue when injected intramuscularly, thus allowing for an effective therapeutic dose to be present for many hours.

In this regard, it should be noted that reference to therapeutically effective dose does not necessarily relate to conventional dosage levels, but does relate to drug levels that achieve an effective therapeutic level at the dose employed, which may be the same level but not at the same frequency of administration. This thus not only significantly reduces the number of doses required to achieve the same effect, it reduces costs, maintenance and health hazards associated with conventional treatment therapies. Additionally, it results in immediate and continued drug release for long periods of time spanning at least 18 hours to even days.

Doses may vary from patient to patient depending on the type and severity of the condition being treated and the drug being administered. Generally, doses of 1 ml to 10 ml may be administered with preferred doses using 4 ml of matrix solution.

The formulations of this invention may be used to treat a variety of animal conditions and physical states. These systems have particular application to pain management, namely the treatment and alleviation of pain associated with any disease, condition or physical state.

Without being limited to the specific pain being treated, the preparations of this invention may treat the following nonlimiting locations or sources of pain: abdominal, such as in appendicitis, dysmenorrhea, musculoskeletal, pelvic, peptic ulcer, psychogenic, and urologic; acute; arm; backache; cancer; cardiac (myocardial ischemia); chest; dental; ear; esophageal; eye; face; head; and neck; in fibromyalgia; foot; and leg; heel; ischemic pain such as in myocardial, peripheral arterial, low back, in mitral valve prolapse, in myocardial infarction, myofascial pain syndrome (fibromyalgia, fibromyositis), neck, neuropathic, neurotransmitter abnormality, nociceptive, and nocturnal pain; pelvic; pericardial; in peripheral arterial disease; phantom limb; pleuritic; polyneuropathy; postmastectomy syndrome; postoperative; psychogenic; in pulmonary embolism; in renal disease, such as colic; root avulsions; shoulder; stump; thalamic; in goes; and toothache.

The phrase "back pain" as used herein refers to all conditions which arise from congenital or traumatic disfunction of physical structures in the back of an animal, such as a human. These include spinal, bone, nerve and muscle origin pain, and include but are not limited to disc damage caused by trauma, disease or congenital defects; degenerative conditions, arthritic disease, accidental injury, nerve impingement such as pinched nerve, inflammatory conditions, neuromuscular diseases, sports injuries and so forth.

Besides chronic and intractable pain where injections of the matrix solution may be required, the present solutions may be used to aid in surgical procedures such as in post surgical pain treatments.

The phrase "surgical procedure" refers to those internal and external procedures where a physician desires to block sensory effects prior to, during or after performing surgical procedures. While being virtually unlimited in scope as in the procedures which can be performed, exemplary external procedures include: cosmetic surgery, hair transplant surgery, procedures for trauma wounds, such as knife and bullet wounds, accidental lacerations; removal of skin growths such as warts, moles and benign or malignant growths, hemorrhoidal removal or other treatments requiring anesthesia. Furthermore, the inventive compositions are able to provide sustained anesthesia effects when used prior to, during or after internal surgical procedures. Again, without being limited to specific surgical procedures, exemplary procedures would involve abdominal, cervical, thoracic or cardiac surgery.

With regard to uses after surgery, the solutions may be used following abdominal, cervical, thoracic or cardiac surgery, whereby multiple layers of tissue are treated with the system, such as during or after the surgical procedure. Such treatments aid in a patient's recovery by not only avoiding addictive drug use such as a morphine drip, but result in the immediate and long term relief of pain to enable rapid rehabilitation.

It has also been unexpectedly found that when the system is administered in a repetitive manner, once the effects of the active drug are reduced in intensity or effectiveness, such repeat treatments may result in a synergistic effect by enhancing the initial term of relief to a period which exceeds the initial time of relief. This is also experienced on subsequent treatments. In this way, the present formulations are able to extend relief or treatment from normally several hours to at least 12 to 24 hours to several days of relief. The use of repeat injections thus enhances drug release which significantly continued tissue damage and may even assist in tissue repair. In addition, the condition being treated is alleviated without significantly modifying motor or sensory function.

Regardless of the route of administration elected, the formulations of the present invention are formulated into pharmaceutically acceptable dosage forms by contentional methods known in the pharmaceutical art.

As discussed above, an effective but nontoxic amount of the system is employed in treatment. The dose regimen for administering drugs or treating various conditions, such as pain as described above, is selected in accordance with a variety of factors including the type, age, weight, sex, and medical condition of the subject, the severity of the pain, the route of administration and the particular complex or combination of drugs employed. Determination of the proper dose for a particular situation is within the skill of the art. Generally, treatment is initiated with smaller dosages which are less than the optimum dose of the compound. Thereafter, the dose is increased by small increments until the optimum effect under the circumstances is reached. For convenience, the total daily dosage may be divided and administered in portions during the day if desired. Generally, amounts of drug may vary from 0.0001% to about 50% by weight of the system when using injections having 2 to 20 ml concentrations and preferably 3 to 10 ml injectable amounts.

Besides treatment of pain, the aqueous system of this invention may be used to treat drug addiction by aiding in the administration of reduced levels of narcotics to addicts as well as using reduced frequency of administration in detoxification and maintenance programs.

In this regard, it should be noted that the withdrawal syndrome from an opioid generally includes symptoms and signs opposite to the drug's pharmacologic effects (e.g., CNS hyperactivity). The severity of the withdrawal syndrome increases with the size of the opioid dose and the duration of dependence. Symptoms begin to appear as early as 4 to 6 hours after withdrawal and reach a peak within 36 to 72 hours for heroin. The initial anxiety and craving for the drug are followed by other symptoms increasing in severity and intensity. A reliable early sign of abstinence is an increased resting respiratory rate, that is greater than 16/min. usually accompanied by yawning, perspiration, lacrimation, and rhinorrhea. Other symptoms include mydriasis, piloerection ("gooseflesh"), tremors, muscle twitching, hot and cold flashes, aching muscles, and anorexia. The withdrawal syndrome in persons who have been taking methadone develops more slowly and overtly less severe than heroin withdrawal, although users may perceive it as worse.

Currently, methadone substitution is the preferred method of opioid withdrawal. Methadone is given orally in the smallest amount that will prevent severe signs of withdrawal but not necessarily all signs. Close observation of the patient is important because the patient's subjective symptoms are unreliable. Many of the symptoms of withdrawal can be mimicked by anxiety states. Generally, 20 mg/day of methadone will block the symptoms of severe withdrawal. Higher doses should be given only on direct observation of the physical signs of withdrawal, since addicts are unreliable in reporting the size of their habits. Doses of 25 to 45 mg can produce unconsciousness if the person has not developed tolerance for heroin or methadone. Once a suppressing dose has been established, it should be reduced progressively by not more than 20% each day. Patients commonly become emotionally upset and frequently request additional medication. Chloral hydrate 500 to 1000 mg may be given orally for several nights to improve sleep. The acute manifestations of withdrawal usually subside within 7 to 10 days, but patients often complain of weakness, insomnia, and a severe pervasive anxiety for several months. Minor metabolic and physiologic effects of withdrawal may persist for up to six months. Conventional procedures treat heroin withdrawal with oral methadone, but the usual low-grade level of dependence can be treated with propoxyphene napsylate or even benzodiazepines, which are not cross-tolerant to opioids. These difficulties would be overcome with use of the present systems.

Unlike methadone, the central α-adrenergic drug clonidine can halt essentially all signs of opioid withdrawal. This probably relates to diminution of central adrenergic outflow secondary to stimulation of central receptors (the same mechanism by which clonidine lowers BP). This theory supports the importance of central adrenergic discharge in the evolution of the opioid withdrawal syndrome. However, clonidine is not a benign drug. Besides causing hypotension and drowsiness, its withdrawal may precipitate restlessness, insomnia, irritability, tachycardia, and headache. Its overall contribution to therapy is minor. Withdrawal is not a difficult problem for patient or clinician; abstinence, which clonidine does not aid, is. The present system would overcome this difficulty.

Experiments with L-acetyl α-methadol (LAAM), a longer-acting synthetic opioid, give hope of help to some addicts and of removing the problem of expensive daily client visits or take-home medication, which ensures some diversion. The culture's loss of faith in methadone maintenance or at least the lessening commitment of public money has diminished the number of treatment facilities and the amount of research given to LAAM.

Unlike the opioids, dependence on anxiolytic and hypnotic drugs raises other difficulties.

Barbiturates and ethanol are strikingly similar in their syndromes of dependence, withdrawal, and chronic intoxication. When intake is reduced below a critical level, a self-limited abstinence syndrome ensures. Symptoms of withdrawal from barbiturates and other sedative-hypnotics can be suppressed completely with a barbiturate. Tolerance develops irregularly and incompletely so that considerable behavioral disturbances and psychotoxicity persist, depending on the drug's pharmacodynamic effects. Some mutual but incomplete cross-tolerance exists between alcohol and the barbiturates as well as the nonbarbiturate sedative-hypnotics, including benzodiazepines.

In susceptible patients, psychologic dependence on the drug may develop rapidly; and, after only a few weeks, attempts to discontinue it exacerbate any initial insomnia and result in restlessness, disturbing dreams, frequent awakening, and feelings of tension in the early morning. The extent of physical dependence is related to dose and the length of time that the drug has been taken; e.g., pentobarbital 200 mg/day may be ingested for many months without significant tolerance developing; 300 mg/day may induce an abstinence syndrome on terminating medication if ingested for more than three moths; and 500 to 600 mg/day may provoke an abstinence syndrome after one month.

The standard procedure for treating dependence on depressants, particularly barbiturates, is to reintoxicate the patient and then withdraw the drug on a strict schedule, being alert for signs of marked withdrawal. Before beginning withdrawal, one can evaluate sedative tolerance with a test dose of pentobarbital 200 mg orally given to the nonintoxicated, fasting patient; 1 to 2 hours later this test dose produces drowsiness or sleep with response to arousal in individuals with no tolerance to pentobarbital. Patients with intermediate levels of tolerance may show some impairment, whereas patients tolerant to 900 mg or more show no signs of intoxication. If the 200-mg dose has no effect, the tolerance level can be determined by repeating the test every 3 to 4 hours with a larger dose. Severe anxiety or agitation may increase the patient's tolerance. Once the 24-hour dose to which the patient is tolerant has been ascertained, that dose of pentobarbital is usually given for 2 or 3 days to stabilize the patient and is then decreased by 10%/day. Use of the present formulation would enable the use of lower doses as well as less frequent dose treatment programs.

Table II from the 16th Edition of the Merck Manual describes the doses of some common sedatives and anxiolytics that have produced physical dependence.

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLE 1

This example demonstrates the formation of a preparation which produces long-acting analgesia when injected intramuscularly.

| MATERIALS | |
|---|---|
| Dilaudid (hydromorphone hydrochloride) | 15 mg |
| Hydroxyethyl cellulose (HEC) | 1.25% |
| Hyaluronate Sodium (HA) | 1.37% |
| Sterile Water | Q.S. |
| Batch Size | 1000 ml |

Into a sterilized glass vessel is added 500 ml of the sterile water which is stirred at 400–600 rpms. Slowly add 13.7 grams of HA having a molecular weight of around 700,000 to 775,000 and a purity described previously.

Allow to stir for 10–20 hours until all the HA polymer has dissolved into the water and a crystal clear viscous solution has formed.

Prepare a 1.25% solution of HEC by adding 12.5 grams of the solid material, under aseptic conditions to 275 ml of sterile water. Allow to dissolve for 1 to 2 hours while stirring. Add the HEC solution to the HA solution and mix for 2 to 4 hours at 490–600 rpms until a homogenous solution is produced. Using aseptic techniques, the solution is then filled into suitable vials or ampules and heat sterilized at 120° C. for 20 minutes. The vials or ampules are then ready for use or storage.

Dissolve 15 mg of Dilaudid in 225 ml of the sterile water and allow to mix for 1–2 hours at 200–400 rpms. Alternatively, commercially available solutions of Dilaudid may be used, such as Dilaudid regular containing 2 milligrams drug per milliliter ampule or Dilaudid HP containing 10 milligrams drug per milliliter ampule. Slowly add the Dilaudid solution to 4 ml of the HA/HEC homogenous solution and mix rapidly.

The resulting product is a clear solution which is free of air bubbles and ready for use.

EXAMPLE 2

The procedure of Example 1 was repeated except that morphine sulfate was used instead of Dilaudid. The morphine sulfate is provided as a solution blended with the matrix solution and may contain 50 mg drug in 1 ml solution blended with 4 ml matrix as well as 100 mg drug in 1 ml solution blended with 4 ml matrix solution.

EXAMPLE 3

The procedure of Example 1 was repeated except that Demerol was used instead of Dilaudid. The Demerol may be conveniently provided in 5 ml ampules containing 50 mg drug. As such doses of 150 mg may be prepared by blending three (3) 5 ml ampules blended with 4 ml of matrix solution. The resulting solution was a clear solution which was free of air bubbles and ready for use.

EXAMPLE 4

This example demonstrates the in vivo use of the Example 1 preparation with various patients suffering from chronic pain.

Run A

MAIN COMPLAINT:

This 48-year-old man is complaining of right-sided cluster headaches which are continuous.

HISTORY:

Mr. T. started to develop cluster headaches about 13 years ago. Initially these were on an occasional basis which became gradually more severe and also more frequent. About six years ago, they became constant, and the patient had severe constant pain which almost totally incapacitated him. He has contemplated suicide. The pain is always mainly behind the right eye. This is a severe pain rated as 10/10. It is also in the right occiput and travels like a rod all the way to behind the right eye. It is associated with tenderness of the right eye lid and lacrimation also rhinorrhea. In going over his early history, it was found that he had his first headache at age 11. This occurred when he fell over the front of the handle bars of his bicycle and landed on his chin. At that time, he developed a headache which was exactly like the clusters he has now. This went away after a few days. Following this, he was involved in two minor motor vehicle accidents, and again on each occasion he developed right-sided cluster headaches which eventually cleared up.

PHYSICAL EXAMINATION:

This reveals a thin man who is somewhat emaciated because of his loss of appetite and severe pain. The right eye lid is constantly drooping, and there is frequent lacrimation from the right eye. There is marked tenderness of the right greater occipital nerve, and less tenderness of the left greater occipital nerve. The right facet joints at C2–3, C3–4 are also tender. Facet diagnostic blocks did not relieve the frontal pain. Occipital blocks have relieved the pain going from the occiput through toward the right eye, but did not entirely relieve the pain in the right eye. The only way this has been relieved is when the right infraorbital or retro-orbital blocks have been done in addition to the occipital blocks.

TREATMENT COURSE:

He has been having weekly blocks of the greater occipital nerve and infratrochlear nerve for two years now. This provide up to 36 hours of relief. The rest of the time, he has such severe pain that he would be totally incapacitated without narcotics. For the past nine months, he has been prescribed Dilaudid 4 mg every four hours. This has to be taken with Benadryl.

USE OF LONG-ACTING POLYMER WITH DILAUDID:

The regular Dilaudid had to be given at least six times a day. However, when Dilaudid 20 mg was mixed with polymer solution of Example 1, about 12 to 16 hours of relief could be obtained. The quality of relief is very good, and he is able to work as a movie director as long as he has pain relief. Previously, he was incapacitated from work by the pain. As indicated, with the plain Dilaudid injection he gets about 2 hours of fairly good relief, but with the polymer solution and Dilaudid he gets 12 to 16 hours of excellent relief. During this time, he is not sleepy or uncomfortable and feels reasonably normal.

Run B

MAIN COMPLAINT:

This 38-year-old woman has complained of pain in the left cervico-occipital temporal area for about ten years.

HISTORY:

In about 1979, Ms. G was abused on a continuing basis by her husband. He would hold her head and hit it against the wall and shake the head. It was at that time that she started to develop left occipitocervical temporal headaches. These were initially infrequent, but in the past ten years they have been almost continuous. She was mistakenly diagnosed as having migraine by her previous physicians.

PHYSICAL EXAMINATION:

This revealed tenderness in the left greater occipital nerve area to 4+, and tenderness of the left facet joints at C2–3 and C3–4. The right greater occipital nerve and facet joints were not especially tender.

INVESTIGATIONS:

1. X-rays of the head and neck were normal.
2. Facet diagnostic blocks at C2–3 and C3–4 on the left were negative.
3. C2 diagnostic block on the left entirely relieved her pain.
4. Greater occipital nerve blocks on the left have relieved her pain.

The diagnosis was as follows: Damage of the occipito-cervical junction possibly the C1–2 facet area. This is causing a left occipital neuralgia.

TREATMENT:

Occipital nerve blocks initially provided 2 to 3 days of relief, but more recently they have only provided one day of relief at a time. She has been getting occipital blocks on a weekly basis which relieved her pain for a couple of days at a time, but more recently one day at a time. In between she has been getting Percocet. However, in the last few months she could not take Percocet because of the gastrointestinal disturbance. She was then put on Dilaudid 4 mg every four hours. This made her very weak, and she could not function after it, and she found she had to take it at least every four hours and sometimes every three hours.

USE OF LONG-ACTING POLYMER WITH DILAUDID:

When 10 mg of Dilaudid was administered with the polymer solution, the pain relief was 16 to 18 hours with each injection. This produced a smooth degree of relief, and she was not nearly as tired or weak as when she took the Dilaudid without polymer solution.

Run C
MAIN COMPLAINT:

This 48-year-old nurse is complaining of severe constant headaches and neck aches. She has had these for about eight years.

HISTORY:

Ms. W. was involved in a motor vehicle accident in 1988. Following this, she was unconscious for a few moments. The next day, she started to develop severe neck aches and headaches which she had never experienced before, and these have not improved over time. Currently she has almost constant severe neck aches which radiate up the back of the head and involve the whole head. Often these are of a throbbing nature. She has had numerous nerve blocks and pain killers over the years to keep her going. Without these treatments, She would be totally incapacitated.

PHYSICAL EXAMINATION:

Examination has revealed marked limitation of movement of the neck to about 30% of normal in both flexion and extension and rotation. The neck muscles are very tender to palpation, and they are swollen. The occipital nerves are tender to 3+ bilaterally, and the face joints are exquisitely tender bilaterally from C2 to C6.

INVESTIGATIONS:

1. X-rays of the neck showed degenerative changes.
2. MRI of the neck has shown disc herniations.

TREATMENTS:

As noted, she has been receiving occipital nerve blocks with analgesics for several years, but she has required increasingly frequent nerve blocks and increasing doses of analgesics. Recently, she had been using fentanyl patches 50 μ/hr. These worked well initially, but ceased to be effective after a few weeks. She was then given Dilaudid 4 mg every four hours by intramuscular injection. She would obtain about two hours of good relief with some degree of relief in the first hour before the injection reached its peak level, and begin partial relief toward the end of the four hours. As noted, there were only two hours of good relief each time.

USE OF LONG-ACTING POLYMER WITH DILAUDID:

She was then given Dilaudid blended with polymer solution as set forth in Example 1 wherein she experienced about 18 hours of good relief. During this time, she was able to function well and could carry out her business functions entirely comfortably without any nausea or tiredness. She found the use of this drug to be very comfortable, and she was able to function normally.

TABLE I

EQUIANALGESIC DOSES OF OPIOID ANALGESICS FOR SEVERE PAIN*

| Drug | IM (mg) | Oral (mg) |
|---|---|---|
| Morphine | 10 | 60† |
| Oxymorphone | 1 | — |
| Hydromorphone | 1.5 | 7.5 |
| Levorphanol | 2 | 4 |
| Methadone | 10 | 20 |
| Oxycodone | 15 | 30 |
| Meperidine | 75 | 300 |
| Codeine | 130 | 200 |
| Pentazocine | 60 | 180 |
| Nalbuphine | 10 | — |
| Butorphanol | 2 | — |

*Equivalences are based on single-dose studies.

TABLE II

| Drug | Doses Producing Dependence (mg/day) | Time Necessary to Produce Dependence (days) | Dosage Equivalent to 30 mg Phenobarbital (mg) |
|---|---|---|---|
| Secobarbital | 500–600 | 30 | 100 |
| Pentobarbital ("yellow jackets") | 500–600 | 30 | 100 |
| Amobarbital ("blues") | 500–600 | 30 | 100 |
| Amobarbital-secobarbital combination ("rainbows") | 500–600 | 30 | 100 |
| Gluethimide | 1250–1500 | 60 | 500 |
| Methyprylon | 1200–1500 | 60 | 300 |
| Ethchlorvynol | 1500–2000 | 60 | 500 |
| Meprobamate | 2000–2400 | 60 | 400 |
| Chlordiazepoxide | 200–300 | 60 | 25 |
| Diazepam | 60–100 | 40 | 10 |
| Methaqualone | 1800–2400 | 30 | 300 |
| Chloral hydrate | 2000–2500 | 30 | 500 |

The invention being thus described, it will be obvious that the same may be varied in many ways. Such variations are not to be regarded as a departure from the spirit and scope of the invention, and all such modifications are intended to be included within the scope of the following claims.

What is claimed is:

1. A long acting analgesic, opioid antagonist, or agonist-antagonist drug composition which comprises:
   a water soluble analgesic, opioid antagonist or agonist-antagonist drug dispersed within a polymer matrix which is solubilized in an aqueous medium, wherein the polymer matrix is comprised of negatively charged polymers selected from the group consisting of hyaluronic acid salts, chondroitin sulfate, and mixtures thereof; and a nonionic polymer selected from the group consisting of carboxymethyl cellulose sodium, hydroxyethyl cellulose, hydroxypropyl cellulose and mixtures thereof, and wherein the ratio of negatively charged polymer to nonionic polymer is 1:0.5 to 2.

2. The composition of claim 1, wherein the negative charged polymer material has a mean average molecular weight below about 800,000.

3. The composition of claim 2, wherein the hyaluronic acid salt is the sodium salt and has a mean average molecular weight of from about 650,000 to about 800,000, a sulphated ash content below about 15% and a protein content below about 5%.

4. The composition of claim 1, wherein the nonionic polymer is hydroxyethyl cellulose.

5. The composition of claim 1, wherein the drug is dispersed within the polymer matrix immediately prior to use.

6. The composition of claim 5, wherein the drug is previously solubilized in an aqueous medium prior to being disbursed in the polymer matrix.

7. A method for making a long acting analgesic, opioid antagonist, or agonist-antagonist injectable drug solution which comprises:

preparing a polymer matrix comprising a negatively charged polymer selected from the group consisting of hyaluronic acid salts, chondroitin sulfate, and mixtures thereof having a mean average molecular weight between about 650,000 and 800,000 and a nonionic polymer selected from the group consisting of carboxymethyl cellulose sodium, hydroxyethyl cellulose, hydroxy- propyl cellulose and mixtures thereof, wherein the ratio of negatively charged polymer to nonionic polymer is 1:0.5 to 2 and the negatively charged polymer is present in an amount of about 0.1% to about 2.0 % by weight of the solution;

solubilizing within the polymer matrix a water-soluble analgesic, opioid antagonist or agonist-antagonist drug by blending the drug with the polymer matrix solution; and recovering the resulting solution.

8. The method of claim 7, wherein the drug is a water-soluble solid which is mixed into the polymer matrix solution prior to use.

9. The method of claim 7, wherein the drug is in the form of a solution prior to mixing with the polymer matrix solution.

* * * * *